(12) United States Patent
Nguyen et al.

(10) Patent No.: US 6,372,513 B1
(45) Date of Patent: Apr. 16, 2002

(54) DEVICE AND PROCESS FOR LATERAL FLOW SALIVA TESTING

(75) Inventors: Lee Huu Nguyen, Irvine; Sholreh Moheb, Yorba Linda, both of CA (US)

(73) Assignee: Ansys Technologies, Inc., Lake Forest, CA (US)

( * ) Notice: Subject to any disclaimer, the term of this patent is extended or adjusted under 35 U.S.C. 154(b) by 0 days.

(21) Appl. No.: 09/552,500

(22) Filed: Apr. 19, 2000

(51) Int. Cl.$^7$ ............................................. G01N 33/48
(52) U.S. Cl. ..................... 436/175; 436/169; 422/58; 422/61
(58) Field of Search .......................... 422/56, 58, 61; 436/164, 166, 169, 175–178

(56) References Cited

U.S. PATENT DOCUMENTS 5,075,078 A * 12/1991 Osikowicz et al. ........... 422/56
5,260,031 A    11/1993 Seymour .................... 422/101

* cited by examiner

Primary Examiner—Lyle A. Alexander
(74) Attorney, Agent, or Firm—Walter A. Hackler

(57) ABSTRACT

A method and device are provided for performing diagnostic testing of an oral fluid specimen. The method generally includes providing a lateral flow test strip having a sample portion and a test portion, evaporating a salt solution on a pad made of glass fiber material, positioning the salt pad on the sample portion of the lateral flow test strip, depositing an oral fluid specimen on the salt pad positioned proximate the sample end of the lateral flow test strip, and allowing proteinaceous materials in the specimen to substantially disassociate from the specimen to facilitate migration of the specimen into the test portion of the lateral flow test strip as a relatively mucin-free specimen. The device includes a lateral flow test strip having a glass fiber salt pad thereon, the lateral flow test strip encased within a housing.

14 Claims, 1 Drawing Sheet

DEVICE AND PROCESS FOR LATERAL FLOW SALIVA TESTING

The present invention generally relates to devices and processes for collection and testing of fluid specimens, and more specifically relates to a device and process for lateral flow testing of oral fluid, for example saliva.

Unlike other forms of fluid specimens such as blood or urine, collection of oral fluid, for example saliva, for diagnostic purposes is complicated by many factors, for example, the low volumes of salivary fluid secreted into the oral cavity, the relatively high viscosity thereof, and the diverse anatomic dispersion of the salivary glands. Most techniques for collection involve the use of capillary tubes, suction into micropipettes, chewing on paraffin or foam, and/or aspiration from the mouth into polypropylene syringes.

Conventional, commercially available lateral flow test strips ( i.e. nitrocellulose strips) have long been used for diagnostic testing of bodily fluids such as urine. These devices are inexpensive and produce reliable results for many applications. These same test strips however are not conventionally used for testing oral fluids such as saliva. It is known that when saliva is applied to a sample pad of a commercially available urine testing lateral flow test strip, the saliva sample does not run. It is believed that this is due to the relatively high concentrations of mucin and other viscous, proteinaceous materials in the specimen.

In addition, testing of salivary specimens has not been extensively developed. Until relatively recently, blood and urine samples were the primary fluids used for testing for disease as well as for evidence of substance abuse. However, it is known that human saliva carries lymphocytes, plasma cells and immunoglobulins that are directly related to the immunoglobulins found in the blood. In addition, saliva carries immunoglobins that are believed to be peculiar to saliva, for example, the antibody known as secretory IgA. Because of the association between immunoglobulins of the blood and saliva, as well as the occurrence of secretory IgA, antigen-antibody tests have been conducted on salival fluid to assess the value of such tests as screening tools for disease.

U.S. Pat. No. 5,922,614 to Cesarczyk describes a Sample Collection Method with Extraction Sleeve. The device is designed for collecting saliva or urine samples using an absorbent, elongate foam member secured in a hollow tube with one portion extending therefrom. The foam member is used to absorb a fluid specimen. The foam member and hollow tube are slidably mounted within a flexible sleeve to cover the foam member as well as provide a means for extracting the fluid from the foam by exerting pressure on the sleeve to compress the foam member to release the fluid. According to Cesarczyk, the device provides an aseptic, easy to use device for collecting a fluid sample such as saliva.

SUMMARY OF THE INVENTION

Accordingly, a method and device are provided for diagnostic testing of an oral fluid, such as saliva or other proteinaceous fluid specimen.

The device generally comprises a housing including well means for receiving a fluid specimen, and testing means, at least partially encased within the housing, for enabling diagnostic testing of the fluid specimen received in the well means. The testing means includes a diagnostic test strip including a sample portion and a test portion for visually indicating test results and test validity.

Advantageously, the device further comprises means for disassociating proteinaceous material from the fluid specimen, for example a membrane or pad having deposited thereon a salt or other known mucinolytic substance known to break down and lower the viscosity of mucin-containing fluids. The pad is preferably comprised of a glass fiber matrix which provides means for filtering the disassociated proteinaceous matter and other particulate material from the specimen. These features of the present invention function to facilitate migration of an originally viscid, mucin containing fluid specimen, such as saliva, without any pretreatment steps. The device allows convenient and rapid testing of a relatively small saliva sample without any need to pre-treat the saliva in order to enable its migration along the test strip.

The salt pad may be positioned to overlay a portion of the sample portion of the test strip. The test strip is encased within the housing such that the salt pad is in fluid communication with the well means.

The present invention further includes a process for lateral flow saliva testing, generally comprising the steps of providing a lateral flow test strip having a sample portion and a test portion, providing a pad having a material capable of disassociating proteinaceous materials in an oral fluid, for example a salt, positioning the pad along the sample portion of the lateral flow test strip, depositing an oral fluid specimen on the pad positioned on the lateral flow test strip, and allowing proteinaceous materials in the specimen to substantially disassociate from the specimen to facilitate migration of the specimen into the test portion of the lateral flow test strip as a relatively mucin-free specimen.

BRIEF DESCRIPTION OF THE DRAWINGS

The device will be more readily understood with respect to the following detailed description when considered in conjunction with the accompanying drawings of which.

DETAILED DESCRIPTION

Figure 1:
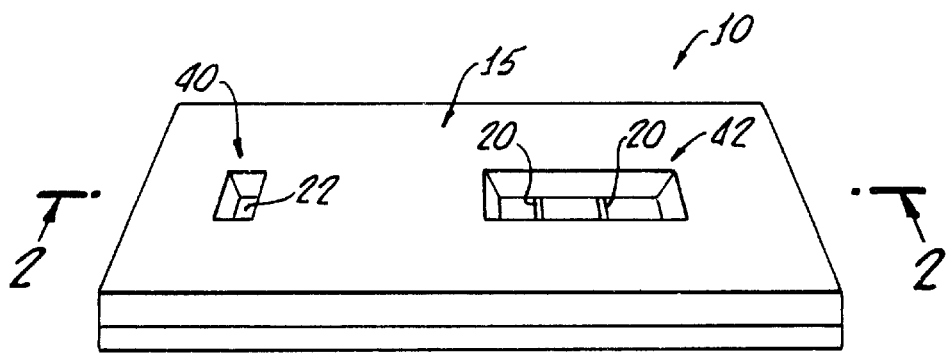
FIG. 1 shows a perspective view of a device, in accordance with the present invention, for lateral flow testing of oral fluid such as saliva, the device including a lateral flow test strip encased within a housing.

Turning now to the Figures, a device 10 for lateral flow saliva testing, in accordance with the invention is shown. The device 10 generally includes a lateral flow test strip 14 encased within a housing 15. Similar to conventional lateral flow test strips, the strip 14 includes a sample pad portion 16 and a test portion 18. The device 10 will be described in greater detail hereinafter.

A process, in accordance with the present invention, for lateral flow testing of saliva or other proteinaceous fluid specimen generally includes the step of providing the lateral flow test strip 14, for example made of a nitrocellulose membrane or other suitable material. The test strip 14 includes a conjugate pad 19 having a suitable detector reagent deposited thereon, and capture zones 20 having suitable capture reagents deposited thereon for indicating presence of a target analyte in the specimen sample and, preferably, an indication of test validity. Reagents may be selected to target analytes found specifically in saliva. Process steps for applying the reagents to the test strip are well known in the art, and may include spraying or jetting the reagents onto the nitrocellulose membrane material.

Figure 2:
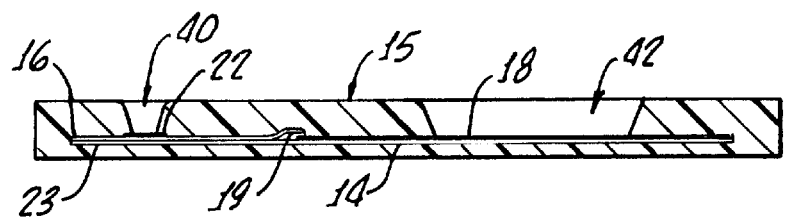
FIG. 2 shows a cross-sectional view of the device, taken along line 2—2 of FIG. 1.
Figure 3:
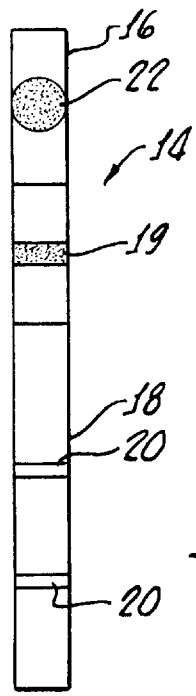
FIG. 3 shows a top view of the lateral flow test strip of the device shown in FIG. 1.

The process in accordance with the invention further comprises the steps of providing a fiber pad 22 (see FIG. 2) having deposited thereon a material capable of disassociating proteinaceous materials in an oral fluid. One suitable material is salt, or sodium chloride. The salt may be deposited on the fiber pad 22 by solution evaporation or other suitable means. The fiber pad 22 is positioned and affixed to the sample portion 16 of the lateral flow test strip 14.

The fiber pad 22 may comprise a fiber matrix material having randomly distributed fibers which create a tortuous path of nominally rated size. Preferably, the fiber pad comprises a die-cut portion of a commercially available glass fiber material having a thickness of about 0.0080 inches. After the salt has been deposited on the glass fiber material, the material is cut, for example in a disc shape with a diameter of about 0.1875 inches. The glass fiber salt disc 22 is then placed on the sample portion 16 of the lateral flow test strip 14. Although a disc shape is shown and described, it is to be appreciated that other shapes and sizes of glass fiber pads are also possible. The glass fiber disc 22, sample pad 16, conjugate pad 19 and adjacent nitrocellulose test portion 18 may be affixed to a support backing 23 and placed in the housing 15.

In one embodiment of the invention, the sample portion 16 of a conventional lateral flow test strip 14 is replaced with a glass fiber sample pad, or is modified to include an additional glass fiber layer. The glass fiber sample pad may be made of the same, commercially available glass fiber material described hereinabove.

For testing a saliva specimen using the example shown, a saliva specimen is applied to the glass fiber salt pad 22. The salt pad 22 breaks down mucin substances in the specimen sample which are subsequently filtered by the glass fibers in the salt pad 22 as well as in the underlying glass fiber sample pad 16 as the specimen migrates toward the lateral flow membrane 14. The specimen sample passes through the conjugate pad 19 where a chemical reaction begins if the analyte is present in the specimen. The specimen a sample then passes into the capture zones 20 and the test can be read.

It is to be understood that the fiber pad 22 effectively facilitates migration of the specimen into the test portion 18 of the lateral flow test strip 14 by both breaking down the proteinaceous material in the specimen and filtering the specimen. More particularly, the salt in the salt pad 22 breaks down the proteinaceous materials in the specimen which are then separated from the less viscous components of the specimen by the glass fiber matrix in the sample pad 16. Thus, after passing through the salt and glass fiber material, the specimen in effect remains as a relatively mucin and particulate free specimen that flows freely and is readily absorbed by the nitrocellulose strip 14.

Advantageously, the process in accordance with the invention requires no specimen pre-treatment procedure. Accordingly, multiple test strips 14 may be prepared in advance, packaged and reserved for future uses. A saliva specimen may be extracted from a subject person and immediately and directly deposited on the salt pad with a pipette or sponge. The salt in the salt disc 22 will cause the proteinaceous materials to separate from the sample, leaving a more freely flowing, lower viscosity sample that can be readily absorbed by, and can migrate along, the strip. Any large, proteinaceous particles in the specimen are filtered out of the specimen by the glass fiber material of the pad 22. The relatively mucin and particulate free sample is then able to migrate along the strip, effectively moving the antibody-marker agents along the strip, and producing a reliable test result in the test results portion 18.

Turning now specifically to FIG. 1, the device 10 for lateral flow testing of a saliva sample is shown as including well means 40 for receiving a saliva specimen by means of a sponge of pipette (not shown). The lateral flow test strip 14 having the salt pad 22 as described above may be positioned in the housing such that the salt pad 22 is visible through the well 40 as shown. The test portion 18 is visible through a window 42 defined in the housing 15 as shown. The housing may be made of molded plastic or other suitable material.

Although there has been hereinabove described a process and device for lateral flow saliva testing, in accordance with the present invention, for the purpose of illustrating the manner in which the invention may be used to advantage, it will be appreciated that the invention is not limited thereto. Accordingly, any and all modifications, variations, or equivalent arrangements which may occur to those skilled in the art should be considered to be within the scope of the invention as defined in the appended claims.

What is claimed is:

1. A method for preparing an oral fluid specimen for diagnostic testing, the method comprising the steps of:

providing a lateral flow test strip having a sample portion and a test portion, said test portion including a detector reagent for diagnostic testing of the fluid specimen;

providing a pad having a material capable of disassociating proteinaceous materials in an oral fluid;

positioning the pad on the sample portion of the lateral flow test strip in a portion enabling the disassociation of proteinaceous material before entering said sample portion;

depositing an oral fluid specimen on the pad positioned proximate the sample end of the lateral flow test strip; and allowing proteinaceous materials in the specimen to substantially disassociate from the specimen to facilitate migration of the specimen from the sample portion and into the test portion of the lateral flow test strip as a relatively mucin-free specimen.

2. The method according to claim 1 wherein the pad comprises a glass fiber pad.

3. The method according to claim 1 wherein the material capable of disassociating comprises a salt.

4. The method according to claim 1 wherein the material is a salt and the step of providing a pad includes the step of evaporating a salt solution on the pad.

5. The method according to claim 4 wherein the pad comprises a glass fiber pad.

6. The method according to claim 1 further comprising the step of placing a filter member over the sample portion of the lateral flow test in order to filter out particulate material from the specimen prior to allowing the specimen to migrate along the test strip.

7. The method according to claim 6 wherein the filter member comprises a glass fiber filter member.

8. A device for diagnostic testing of oral fluid such as saliva, the device comprising:

a housing including well means for receiving a fluid specimen;

testing means, including an absorbent lateral flow test strip, encased within the housing, for enabling diagnostic testing of the fluid specimen received in the well means; and fiber pad means, in fluid communication with the well means and the test strip, for disassociating proteinaceous material from the fluid specimen and filtering particulate material from the fluid specimen.

9. The device according to claim 8 wherein the fiber pad means comprises a salt pad.

10. The device according to claim 8 wherein the fiber pad means comprises a glass fiber pad.

11. The device according to claim 8 wherein the fiber pad means comprises a glass fiber pad having a salt deposited thereon.

12. The device according to claim 8 wherein the fiber pad means comprises a glass fiber pad including and evaporated salt solution.

13. A device for diagnostic testing of oral fluid such as saliva, the device comprising:

testing means, including an absorbent lateral flow test strip having a sample portion and a test portion, for enabling diagnostic testing of the fluid specimen received on the sample portion;

means, comprising a salt deposit in fluid communication with the sample portion, for disassociating particulate proteinaceous material from the fluid specimen; and fiber pad means, disposed on the lateral flow test strip, for filtering the particulate material from the fluid specimen to facilitate migration of the fluid specimen from the sample portion to the test portion.

14. The device according to claim 13 wherein the fiber pad means comprises a glass fiber membrane.

* * * * *